United States Patent
Podany et al.

[11] Patent Number: 6,013,048
[45] Date of Patent: Jan. 11, 2000

[54] ULTRASONIC ASSISTED LIPOSUCTION SYSTEM

[75] Inventors: Vaclav O. Podany, New Fairfield, Conn.; Stephen A. Bollinger, Tucson, Ariz.

[73] Assignee: Mentor Corporation, Santa Barbara, Calif.

[21] Appl. No.: 08/965,799

[22] Filed: Nov. 7, 1997

[51] Int. Cl.⁷ .............................. A61B 17/20; A61M 1/00
[52] U.S. Cl. ................................. 604/22; 604/35
[58] Field of Search .................. 604/20–22, 27, 604/30, 35, 65, 246, 500, 902, 909; 606/169–171

[56] References Cited

U.S. PATENT DOCUMENTS

| | | | |
|---|---|---|---|
| Re. 28,752 | 3/1976 | Balamuth et al. | 31/116 |
| 3,213,537 | 10/1965 | Balamuth et al. | 32/28 |
| 3,589,363 | 6/1971 | Banko et al. | 128/276 |
| 3,693,613 | 9/1972 | Kelman | 128/24 |
| 3,735,755 | 5/1973 | Eggleton et al. | 128/24 |
| 3,896,811 | 7/1975 | Storz | 128/328 |
| 3,902,495 | 9/1975 | Weiss et al. | 128/276 |
| 3,924,335 | 12/1975 | Balamuth et al. | 32/58 |
| 3,990,452 | 11/1976 | Murry et al. | 128/305 |
| 4,040,414 | 8/1977 | Suroff | 128/24 |
| 4,063,557 | 12/1977 | Wuchinich et al. | 128/276 |
| 4,136,700 | 1/1979 | Broadwin et al. | 128/305 |
| 4,428,748 | 1/1984 | Peyman et al. | 604/22 |
| 4,587,958 | 5/1986 | Noguchi et al. | 128/24 |
| 4,642,581 | 2/1987 | Erickson | 331/143 |
| 4,768,796 | 9/1988 | Kreizman et al. | 128/24 A |
| 4,808,154 | 2/1989 | Freeman | 604/22 |
| 4,869,256 | 9/1989 | Kanno et al. | 128/660.04 |
| 4,922,902 | 5/1990 | Wuchinich et al. | 604/22 |
| 4,931,047 | 6/1990 | Broadwin et al. | 604/22 |
| 5,026,387 | 6/1991 | Thomas | 606/169 |
| 5,151,085 | 9/1992 | Sakurai et al. | 604/22 |
| 5,163,433 | 11/1992 | Kagawa et al. | 128/660.01 |
| 5,176,677 | 1/1993 | Wuchinich | 606/46 |
| 5,209,719 | 5/1993 | Baruch et al. | 604/22 |
| 5,279,547 | 1/1994 | Costin | 604/22 |
| 5,391,144 | 2/1995 | Sakurai et al. | 604/22 |
| 5,419,761 | 5/1995 | Narayanan et al. | 604/22 |
| 5,421,829 | 6/1995 | Olichney et al. | 606/170 |
| 5,462,522 | 10/1995 | Sakurai et al. | 604/22 |
| 5,630,799 | 5/1997 | Beiser et al. | 604/66 |
| 5,685,840 | 11/1997 | Schechter et al. | 604/22 |
| 5,823,990 | 10/1998 | Henley | 604/22 |
| 5,871,493 | 2/1999 | Sjostrom et al. | 606/180 |

FOREIGN PATENT DOCUMENTS

| | | |
|---|---|---|
| 61-159952 | 7/1986 | Japan . |
| 61-191350 | 8/1986 | Japan . |
| WO 92/09238 | 6/1992 | WIPO . |
| WO 95/03740 | 2/1995 | WIPO . |

OTHER PUBLICATIONS

Sonokinetics Corporation, "A new purely Ultrasonic solution to bone cement removal", Jan. 1994.

Valleylab Inc., "Valleylab CUSA System 200 Console", Jan. 1995.

SMEI srl, "smei Surgical Medical Aesthetic Supplies".

Sebbin Laboratoires, "LIPO–SONS An Ultrasonic Lipo Aspiration Device".

Primary Examiner—Corrine McDermott
Assistant Examiner—Michael J. Hayes
Attorney, Agent, or Firm—Fish & Richardson P.C.

[57] ABSTRACT

An ultrasonic liposuction system includes a handpiece having a transducer for converting electrical energy into mechanical energy in the form of ultrasonic vibrations; an ultrasonic generator electrically connected to the handpiece for supplying the electrical energy to the transducer; an aspirator connected in fluid communication with the handpiece for providing aspiration at a surgical site; and a user interface, disposed on the hand piece, and coupled to the ultrasonic generator and the aspirator for generating control signals therefor.

44 Claims, 10 Drawing Sheets

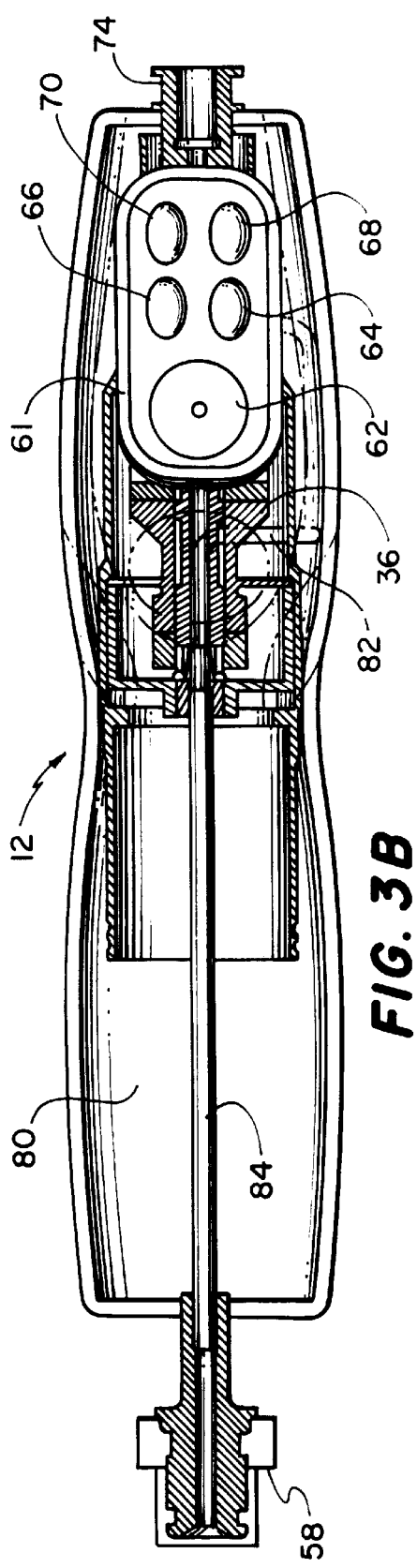
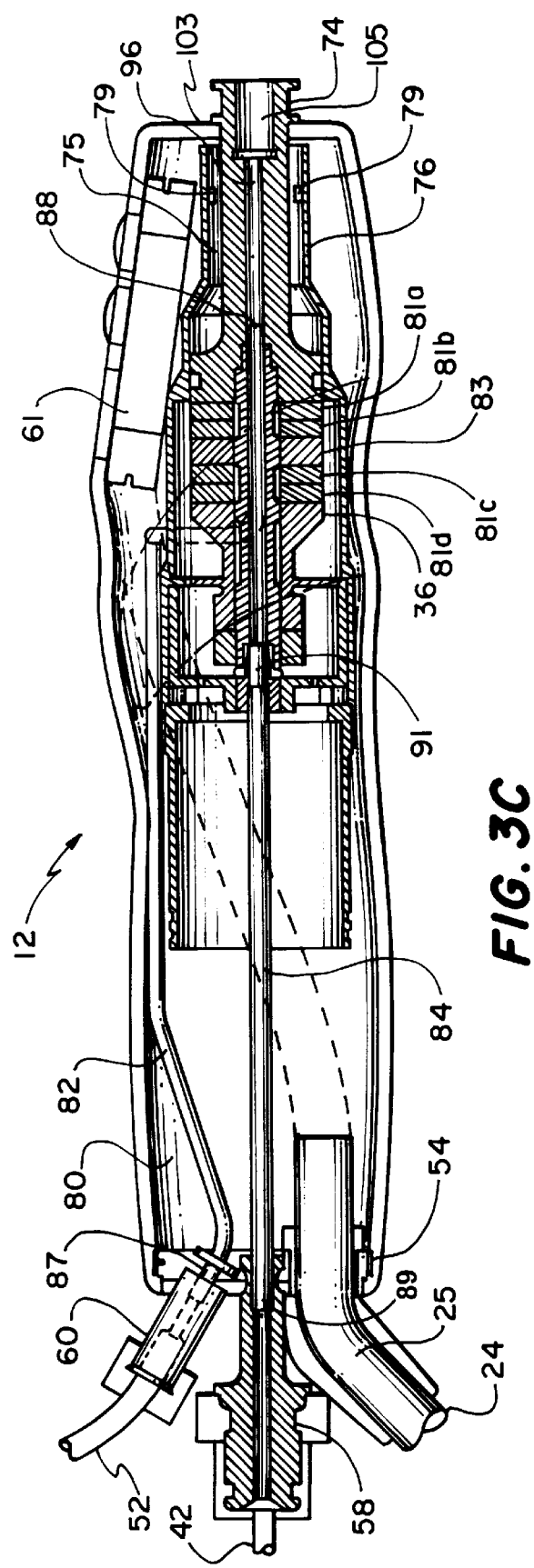
FIG. 3B
FIG. 3C

ULTRASONIC ASSISTED LIPOSUCTION SYSTEM

BACKGROUND OF THE INVENTION

This invention relates to devices which generate ultrasonic vibrations to treat tissue, for example, adipose tissue.

Ultrasonic assisted liposuction is typically conducted using an ultrasonically vibrating cannula extending through a portal to a surgical site. The surgeon carefully manipulates the ultrasonically vibrating cannula to treat tissue to be removed while avoiding other bodily tissue such as muscles, body organs and blood vessels. Liposuction devices are known in which the cannula has a lumen and suction is applied to the lumen to remove treated adipose tissue. It is also known to supply irrigation solution to the surgical site during or prior to surgery.

SUMMARY OF THE INVENTION

In general, according to one aspect of the invention, an ultrasonic liposuction system includes a handpiece having a transducer for converting electrical energy into mechanical energy in the form of ultrasonic vibrations; an ultrasonic generator electrically connected to the handpiece for supplying the electrical energy to the transducer; an aspirator connected in fluid communication with the handpiece for providing aspiration at a surgical site; and a user interface coupled to the ultrasonic generator and the aspirator for generating control signals therefor.

Embodiments of this aspect of the invention may include one or more of the following features.

A fluid source is connected in fluid communication with the handpiece for providing a fluid at the surgical site. The user interface is coupled to the fluid source for generating control signals therefor. The user interface includes a control pad located on the handpiece for generating the control signals. The user interface includes input devices for generating start/stop control signals for the ultrasonic generator and for generating control signals to cause the ultrasonic generator to vary an amplitude of the ultrasonic vibrations. A first button generates ultrasonic amplitude increase control signals and a second button generates ultrasonic amplitude decrease control signals. An ultrasonic generator control line connects the user interface to the ultrasonic generator and transmits control signals to the ultrasonic generator.

The user interface includes an input device for generating start/stop control signals for the fluid source. A fluid source control line connects the user interface to the fluid source and transmits control signals to the fluid source. Another input device of the user interface generates start/stop control signals for the aspirator. An aspirator control line connects the user interface to the aspirator and transmits control signals to the aspirator.

The user interface includes a foot control device for generating control signals for the ultrasonic generator, fluid source, and aspirator. An ultrasonic generator control line, a fluid source control line, and an aspirator control line are connected to the foot control device and transmit control signals to the ultrasonic generator, fluid source, and aspirator, respectively. The fluid source is an infiltrator.

The ultrasonic generator has a front panel with an amplitude display, an amplitude adjustment switch, a power on/off switch, an ultrasonic generator on/off switch, and a connector for connecting the ultrasonic generator to the handpiece. The aspirator has a front panel with a power on/off switch, an aspiration start/stop button, a vacuum level control button, a vacuum level display, and a connector for connecting the aspirator to the ultrasonic generator. The fluid source has a front panel with a power on/off switch, a fluid source start/stop button, a fluid source flow rate control button, a fluid source flow rate display, and a connector for connecting the fluid source to the ultrasonic generator.

The ultrasonic transducer includes a piezoelectric crystal. The ultrasonic vibrations produced by the system are in the range of about 15 KHz to 60 KHz; preferably, about 27 KHz. The fluid source includes a pump. The aspirator includes a canister which collects matter removed from the surgical site, and a filter located downstream of the canister. A feedback system controls the frequency and amplitude of the ultrasonic vibrations.

In another aspect, the invention features a handheld surgical apparatus for use with an ultrasonic liposuction system. The handheld surgical apparatus includes a handpiece electrically connected to an ultrasonic generator and an aspirator, and configured to receive an ultrasonic probe; an ultrasonic transducer disposed within the handpiece for converting electrical energy from the ultrasonic generator into mechanical energy in the form of ultrasonic vibrations; an aspirator conduit disposed within the handpiece; and a user interface coupled to the ultrasonic generator and the aspirator for generating control signals therefor.

Embodiments of this aspect of the invention may include one or more of the following features. The aspirator conduit has a proximal end terminating in an aspirator connector for connecting with the aspirator and a distal end configured for connection in fluid communication with the probe so that matter can be removed from a surgical site by suction provided by the aspirator.

The handpiece includes a fluid conduit having a proximal end terminating in a fluid source connector for connecting with a fluid source, and a distal end configured to provide a fluid supplied by the fluid source to the probe, for example, a cannula, and subsequently to the surgical site.

In another aspect, the invention features a method of controlling an ultrasonic liposuction system including a user interface coupled to an ultrasonic generator and an aspirator for generating control signals therefor. Controlling the system includes activating the ultrasonic generator with a first input device on the user interface, and activating the aspirator with a second input device on the user interface to provide suction.

The amplitude of the ultrasonic generator is controlled with a third input device on the user interface. A fluid source is controlled by with fourth input device on the user interface.

In another aspect, the invention features a method of performing liposuction by advancing a probe and a sheath disposed coaxially about the probe to a surgical site, ultrasonically vibrating the probe to treat tissue at the surgical site by activating an ultrasonic generator connected to the probe, aspirating the surgical site by applying suction to the surgical site to remove the treated tissue by activating an aspirator connected to the probe, and controlling the activation of the ultrasonic generator and the aspirator with a user interface coupled to the ultrasonic generator and the aspirator.

Aspects of this invention may include supplying a fluid to the surgical site by activating a fluid source connected to the probe such that the fluid flows in a space defined between the probe and the sheath. The user interface is coupled to the fluid source to activate the supplying of the fluid.

Among other advantages, the ultrasonic liposuction system of the present invention enables the surgeon to control the ultrasonic generator, fluid source, and aspirator with the same handheld apparatus used to perform the surgery. This centralized control enables the surgeon to adjust surgical parameters during the procedure without the need to make adjustments on the individual consoles themselves.

Other features and advantages of the invention will become apparent from the following detailed description and from the claims.

BRIEF DESCRIPTION OF THE DRAWINGS

FIG. 3B is a partial top cross-sectional view of the handpiece of FIG. 3A; FIG. 3C is a side cross-sectional view of the handpiece of FIG. 3A.

DETAILED DESCRIPTION

Figure 1:
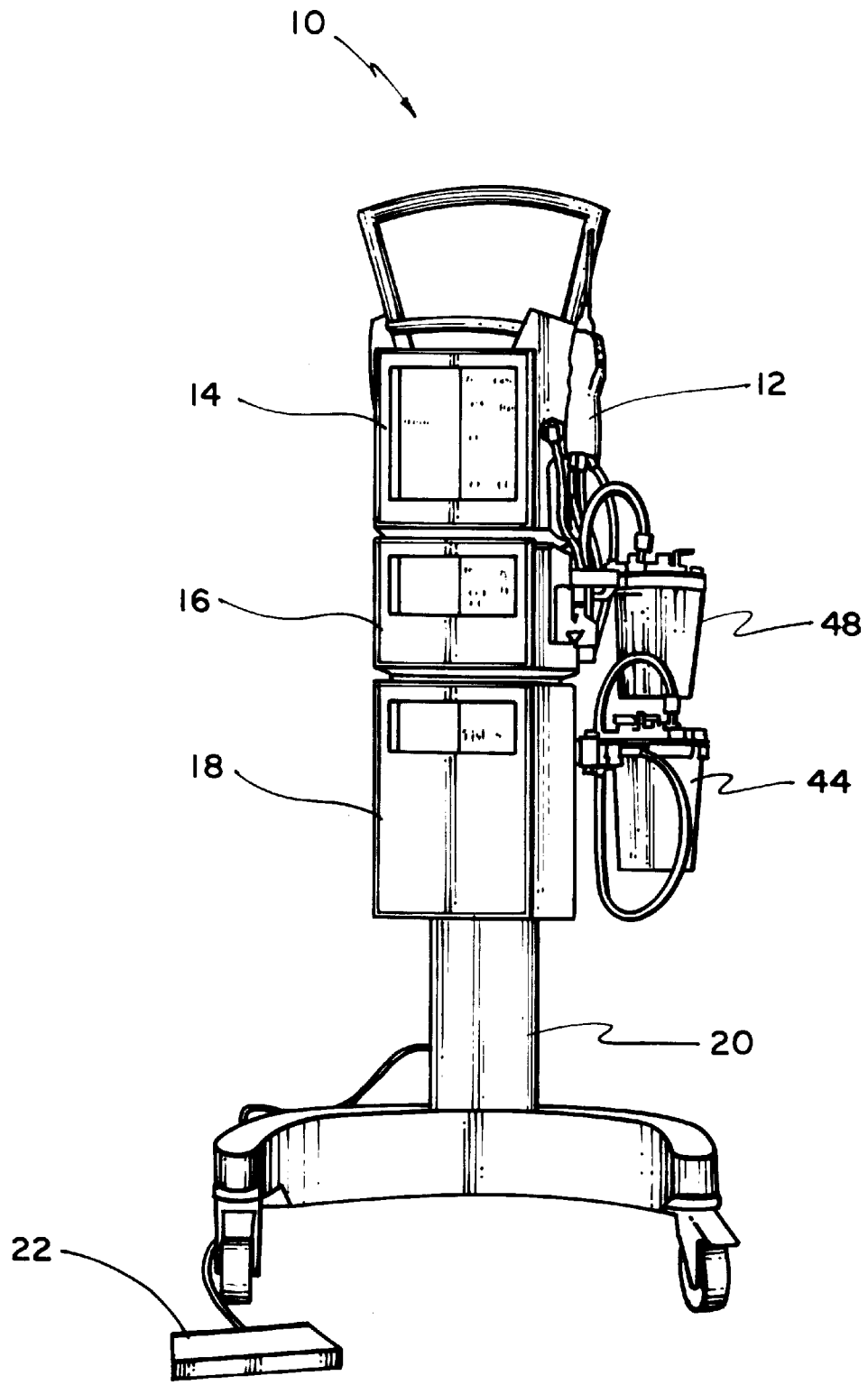
FIG. 1 is a diagrammatic illustration of an ultrasonic liposuction system according to the invention.

With reference to FIG. 1, an ultrasonic liposuction system 10 for removing adipose tissue from a human or other animal body includes a handpiece 12, an ultrasonic generator 14, an infiltrator/irrigator 16, and an aspirator 18 mounted on a mobile cart 20. The components of system 10 are integrated and centrally controlled by electrically connecting handpiece 12 with ultrasonic generator 14, infiltrator/irrigator 16, and aspirator 18. Handpiece 12 is further in fluid communication with infiltrator/irrigator 16 and aspirator 18.

The surgeon controls the operation of ultrasonic generator 14, infiltrator/irrigator 16 and aspirator 18 with a user interface, e.g. a control pad 61 (FIG. 3A), on handpiece 12. Additionally or alternatively, a two-pedal foot control device 22 which is electrically connected to ultrasonic generator 14, infiltrator/irrigator 16 and aspirator 18 can be used to control ultrasonic generator 14, infiltrator/irrigator 16 and aspirator 18.

Ultrasonic generator 14 provides energy to a cannula 38 (described below) attached to handpiece 12 causing cannula 38 to ultrasonically vibrate. The surgeon places cannula 38 at a surgical site within the body to treat adipose tissue. Aspirator 18 provides suction to the surgical site to remove the treated tissue. The treated tissue is collected in a waste canister 44. A backup canister 48 is also provided in the event that waste canister 44 becomes full.

Irrigation and/or infiltration solution is provided by infiltrator/irrigator 16. Infiltration solution generally includes a saline solution with drugs for pain relief and blood loss control and is delivered to the area of tissue to be treated prior to the ultrasonic procedure. The amount of infiltration solution provided is generally about equal to the amount of treated tissue to be removed. Irrigation solution generally includes only a saline solution and is delivered to the surgical site during the ultrasonic procedure.

Figure 2:
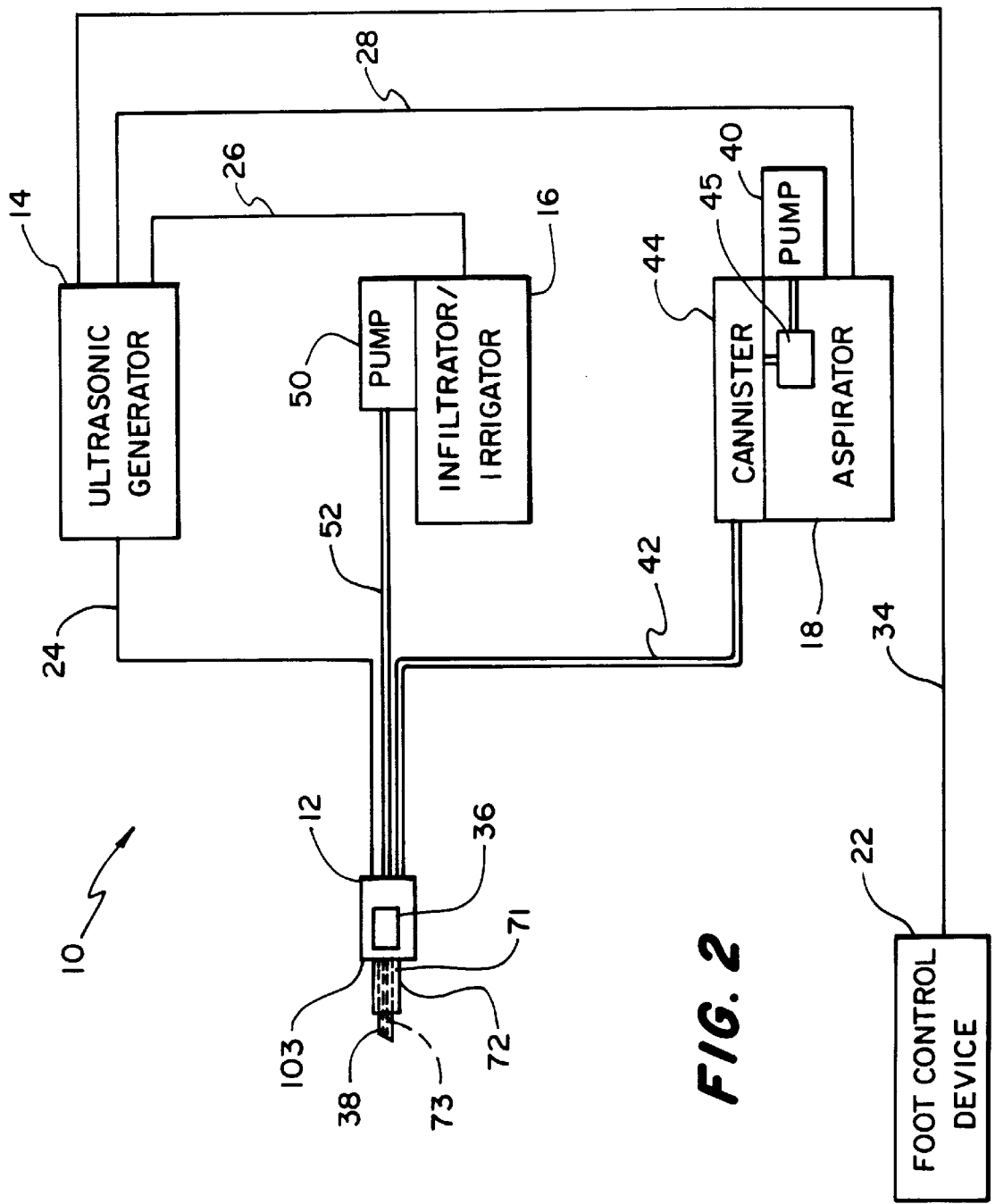
FIG. 2 is a component schematic of the ultrasonic liposuction system of FIG. 1.

Referring to FIG. 2, handpiece 12 is electrically connected to ultrasonic generator 14 by a control line 24, and ultrasonic generator 14 is in turn electrically connected to infiltrator/irrigator 16 and aspirator 18 by control lines 26 and 28, respectively. Foot control device 22 is electrically connected to ultrasonic generator 14 with a control line 34 and through ultrasonic generator 14 to infiltrator/irrigator 16 and aspirator 18 by respective control lines 26 and 28 for providing control of ultrasonic generator 14, infiltrator/irrigator 16 and aspirator 18 with the surgeon's foot.

A transducer 36 located in handpiece 12 transforms electrical energy supplied by ultrasonic generator 14 to mechanical energy in the form of ultrasonic vibrations. The vibrations are transmitted to cannula 38 attached to a distal end 103 of handpiece 12. A sheath 72 is disposed about cannula 38 and connected to distal end 103 of handpiece 12. A region 71 is defined between cannula 38 and sheath 72.

A flow tube 42 connects handpiece 12 in fluid communication with aspirator 18. A pump 40 of aspirator 18 creates a vacuum to draw treated tissue from the surgical site through a lumen 73 in cannula 38 and through flow tube 42. The treated tissue collects in canister 44. A filter 45 positioned between canister 44 and pump 40 prevents treated tissue from flowing into pump 40. A flow tube 52 connects handpiece 12 in fluid communication with infiltrator/irrigator 16. A peristaltic pump 50 of infiltrator/irrigator 16 supplies infiltration/irrigation solution through flow tube 52 and through region 71 between cannula 38 and sheath 72 to the surgical site.

Figure 3A:
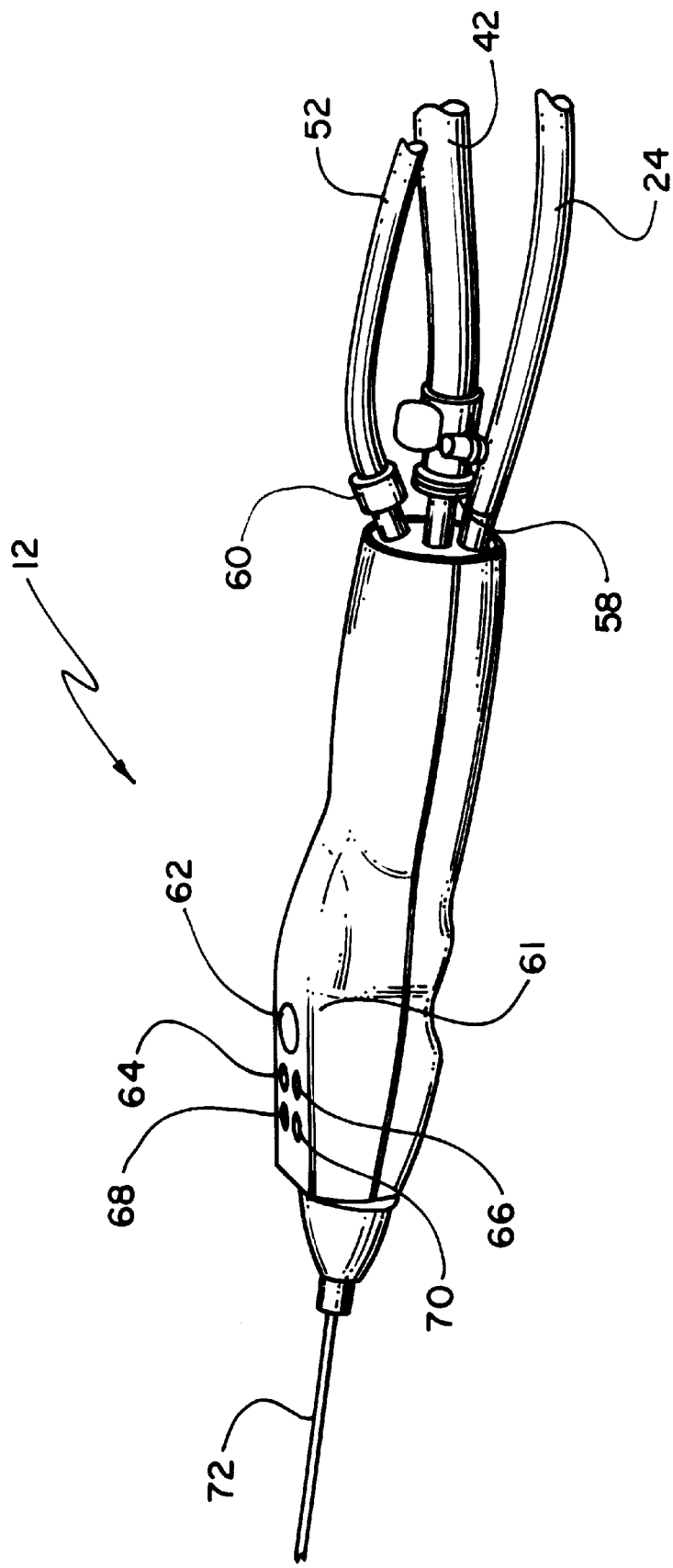
FIG. 3A shows a handpiece of the ultrasonic liposuction system of FIG. 1.

Referring now to FIGS. 3A–3C, control line 24 includes a distal end 25 secured to handpiece 12 by a support 54. Aspirator flow tube 42 and infiltrator/irrigator flow tube 52 are connected to handpiece 12 by quick-release connectors 58 and 60, respectively.

Control pad 61 of handpiece 12 provides the surgeon with a central source for control of ultrasonic generator 14, infiltrator/irrigator 16 and aspirator 18. Control pad 61 includes an ultrasonic generator start/stop button 62, ultrasonic amplitude increase and decrease buttons 64 and 66, respectively, an infiltrator/irrigator start/stop button 68, and an aspirator start/stop button 70. Start/stop button 62 controls the activation and deactivation of ultrasonic generator 14, and amplitude increase and decrease buttons 64 and 66 vary the magnitude of the electrical energy provided by ultrasonic generator 14. Similarly, respective start/stop buttons 68 and 70 activate and deactivate infiltrator/irrigator 16 and aspirator 18. All control signals are sent to ultrasonic generator 14, and from ultrasonic generator 14 to infiltrator/irrigator 16 and aspirator 18.

Figure 3D:
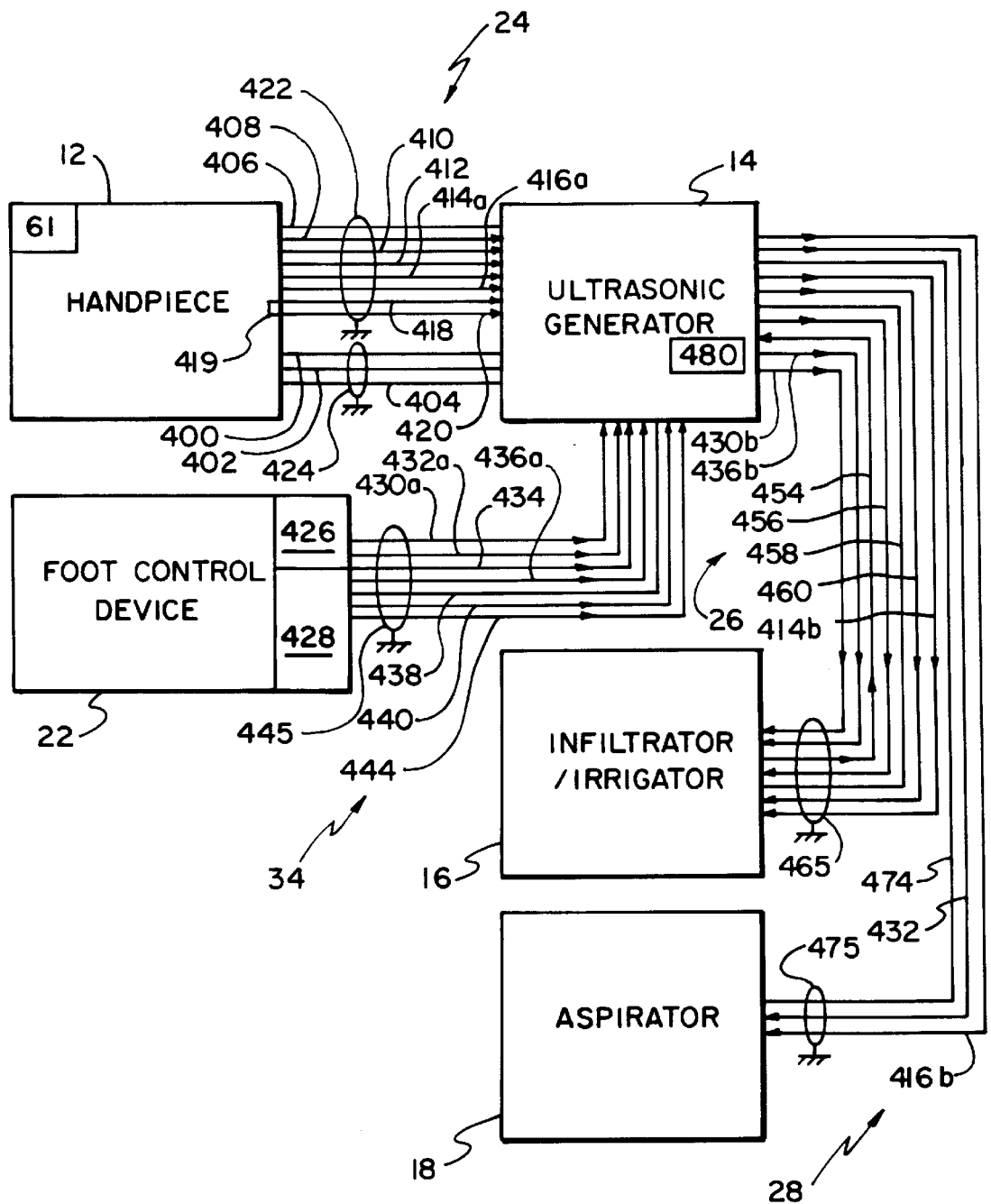
FIG. 3D is a block diagram of electrical connections of the ultrasonic liposuction system of FIG. 1.

Referring to FIG. 3D, control line 24 connected between handpiece 12 and ultrasonic generator 14 includes a transducer power supply line 400 and two transducer ground lines 402, 404 surrounded by an electrical ground shield 424. Transducer supply line 400 transmits electrical energy from ultrasonic generator 14 to transducer 36 of handpiece 12. Ultrasonic generator start/stop input signals from start/stop button 62 of control pad 61 are transmitted to ultrasonic generator 14 by ultrasonic start/stop line 412. Signals from amplitude increase button 64 and amplitude decrease button are transmitted to ultrasonic generator 14 via amplitude increase and decrease lines 408 and 410, respectively.

Irrigator start/stop control signals from start/stop button 68 of control pad 61 are transmitted to infiltrator/irrigator 16 via irrigator start/stop line 414a, ultrasonic generator 14, and irrigator start/stop line 414b. Aspirator start/stop control signals sent from start/stop button 70 of control pad 61 are transmitted to aspirator 18 through aspirator start/stop line 416a, ultrasonic generator 14, and aspirator start/stop line 416b.

Two handpiece ID lines 418, 420 are connected together by a jumper 419 in handpiece 12 to indicate to ultrasonic generator 14 that handpiece 12 is properly connected to ultrasonic generator 14. An additional common ground line 406 connects handpiece 12 to ultrasonic generator 14.

Common line 406, ID lines 418 and 420, ultrasonic generator start/stop line 412, amplitude increase and decrease lines 408 and 410, irrigator start/stop line 414a, and aspirator start/stop line 416a are surrounded by a ground shield 422.

Foot control device 22 includes two pedals 426, 428. Pedal 426 provides control signals to ultrasonic generator 14, the irrigator component of infiltrator/irrigator 16, and aspirator 18. When pedal 426 is depressed, ultrasonic generator 14, infiltrator/irrigator 16, and aspirator 18 are simultaneously activated. Ultrasonic generator 14, infiltrator/irrigator 16, and aspirator 18 are deactivated by releasing pressure from pedal 426. Control line 34 connected between foot control device 22 and ultrasonic generator 14 includes an ultrasonic generator start/stop line 434 for transmitting start/stop control signals to ultrasonic generator 14. Irrigator start/stop signals are transmitted to infiltrator/irrigator 16 through irrigator start/stop line 430a, ultrasonic generator 14, and irrigator start/stop line 430b. Aspirator start/stop signals are sent to aspirator 18 via aspirator start/stop line 432a, ultrasonic generator 14, and start/stop line 432b.

Pedal 428 is used to activate and deactivate the infiltrator component of infiltrator/irrigator 16. Infiltrator control signals are sent from pedal 428 to infiltrator/irrigator 16 through infiltrator start/stop line 436a, ultrasonic generator 14, and infiltrator start/stop line 436b.

Control line 34 also includes a common ground line 438, a connect line 440, and a dual-pedal ID line 444. Connect line 440 transmits a signal from foot control device 22 to ultrasonic generator 14 to indicate that foot control device 22 is properly connected. Dual-pedal ID line 444 transmits an additional signal to ultrasonic generator 14 to indicate that foot control device 22 is connected. Alternatively, a single-pedal foot controller (not shown) can be used instead of foot control device 22 if foot control of only the infiltrator is desired.

Ultrasonic generator start/stop line 434, irrigator start/stop line 430a, aspirator start/stop line 432a, infiltrator start/stop line 436a, common ground line 438, connect line 440, and dual-pedal ID line 440 are covered by a ground shield 445.

Control line 26 also includes a common ground line 458. A signal to indicate that infiltrator/irrigator 16 is properly connected is transmitted to ultrasonic generator 14 by a infiltrator/irrigator ID line 454. In turn, an ultrasonic generator ID line 456 transmits a signal to infiltrator/irrigator 16 that ultrasonic generator 14 is electrically connected to infiltrator/irrigator 16. A switch 480 on ultrasonic generator 14 is set by the user to activate either the irrigator component or the infiltrator component of infiltrator/irrigator 16. The signal from switch 480 is sent to infiltrator/irrigator 16 via infiltrator/irrigator mode select line 460.

Irrigator start/stop line 414b, irrigator start/stop line 430b, infiltrator start/stop line 436b, infiltrator/irrigator ID line 454, ultrasonic generator ID line 456, common ground line 458, and infiltrator/irrigator mode select line 460 are covered with a ground shield 465.

Control line 28 includes common ground line 474. Common ground line 474, aspirator start/stop line 416b, and aspirator start/stop line 432b are surrounded with a ground shield 475.

As stated above, the transmission of control signals between handpiece 12 and ultrasonic generator 14, infiltrator/irrigator 16 and aspirator 17 is facilitated by electrical connections. It is also possible to optically, magnetically, pneumatically or mechanically connect handpiece 12 to ultrasonic generator 14, infiltrator/irrigator 16 and aspirator 17 for transmitting control signals between the devices, i.e. handpiece 12, ultrasonic generator 14, infiltrator/irrigator 16 and aspirator 18. Further, foot control device 22 may be optically, magnetically, pneumatically or mechanically connected to ultrasonic generator 14, infiltrator/irrigator 16 and aspirator 18.

Referring again to FIGS. 3B and 3C, handpiece 12 defines a hollow region 80 within which are disposed an infiltration/irrigation tube 82, an aspiration tube 84, and transducer 36. A proximal end 87 of infiltration/irrigation tube 82 is attached to connector 60 placing infiltration/irrigation tube 82 in fluid communication with flow tube 52. A distal end 88 of infiltration/irrigation tube 82 opens into a channel 75 defined between transducer 36 and a housing 76. Channel 75 communicates with region 71 between cannula 38 and sheath 72.

Aspiration tube 84 includes a proximal end 89 attached to connector 58 and a distal end 91 terminating in fluid communication with a bore 96 of transducer 36. Transducer 36 has a connector 74 located at distal end 103 of handpiece 12 defining an opening 105 which places bore 96 in flow communication with lumen 73 of cannula 38 when cannula 38 is attached to connector 74.

Transducer 36 includes four annular ceramic disks 81a, 81b, 81c, 81d, and an annular heat sink 83. Ceramic disks 81a–81d are piezoelectric crystals. The electrical energy supplied to transducer 36 causes ceramic disks 81a–d to generate ultrasonic vibrations with a frequency between 15 KHz to 60 KHz; preferably the frequency is about 27 KHz. Heat sink 83 withdraws heat generated from the vibrating disks to maintain transducer 36 at a proper operating temperature.

The basic idea of liquefying or melting adipose tissue with ultrasonic vibrations is described in Parisi et al., U.S. Pat. No. 4,886,491, titled LIPOSUCTION PROCEDURE WITH ULTRASONIC PROBE, incorporated by reference herein.

Figure 4A:
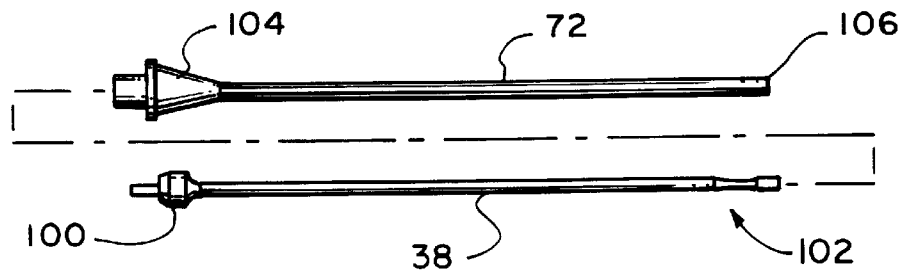
FIG. 4A shows a cannula and sheath used with the handpiece of FIG. 3A.
Figure 4B:
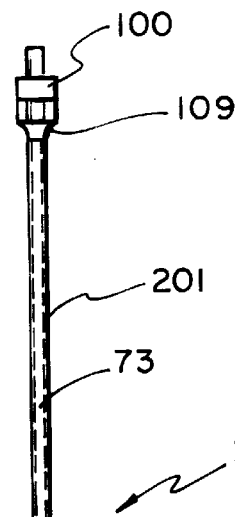
FIG. 4B is an expanded side view of the cannula of FIG. 4A.
Figure 4C:
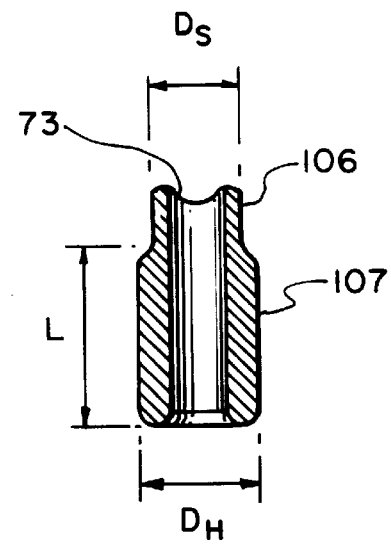
FIG. 4C is a side cross-sectional view of a head portion of the cannula of FIG. 4B.

Referring to FIGS. 4A–4C, cannula 38 includes a proximal end 100 configured to releasably engage with connector 74 of handpiece 12, and a distal end portion 102 from which pressure waves produced by the ultrasonic vibrations are transmitted to the surgical site. Sheath 72 includes a proximal end 104 configured for engagement with a of pins 79, spaced apart by about 180°, of housing 76 such that channel 75 in handpiece 12 and region 71 defined between cannula 38 and sheath 72 are in fluid communication. Lumen 73 extends from proximal end 100 of cannula 38 to distal end 102. The treated tissue flows through lumen 73 of cannula 38 to remove the treated tissue during aspiration of the surgical site.

Cannula 38 includes, for example, a first region 201 of constant outer diameter, a second region, shank 106, of decreased outer diameter, and a third region, enlarged head 107, having a diameter approximately equal to that of first region 201. A cannula with an enlarged head is described in Manna et al., U.S. Pat. No. 5,527,273, titled ULTRASONIC LIPECTOMY PROBE AND METHOD OF MANUFACTURE, incorporated by reference herein. A step-down section 109 between proximal end 100 and first region 201, and another step-down section 110 between first region 201 and shank 106 amplify the ultrasonic vibrations from proximal end 100 to head 107. The outer diameter of cannula 38 increases from shank diameter $D_s$ of, e.g. about 0.143 inches, to a head outer diameter $D_h$ of, e.g. about 0.200 inches. Head 107 extends over a length L of, e.g. about 0.276 inches.

Figure 4D:
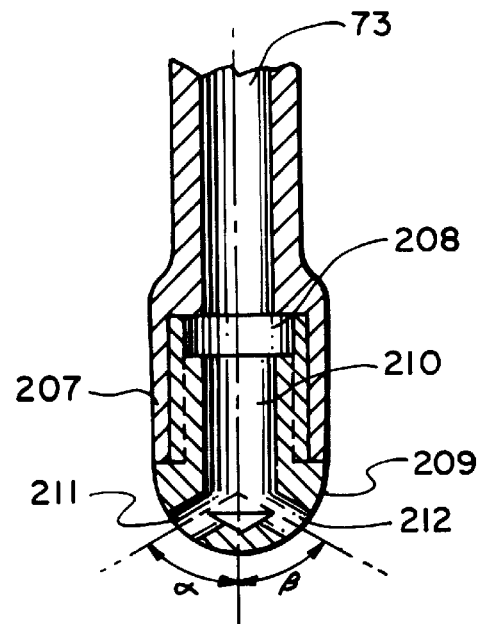
FIG. 4D is a side cross-sectional view of an alternative embodiment of a head portion of a cannula that can be used with the handpiece of FIG. 3A.

Referring to FIG. 4D, an alternative cannula design includes an enlarged head 207 defining an enlarged opening 208 at the distal end of cannula lumen 73. A bullet-shaped plug 209 is received within opening 208. Plug 209 defines a bore 210 which communicates with lumen 73. A pair of inlet bores 211, 212 of plug 209 intersect bore 210 at angles α, β, respectively, of about 60°, from an axis 213. Plug 209 is secured to head 207 with a machine thread or by welding, brazing, gluing, or press fitting.

Figure 5:
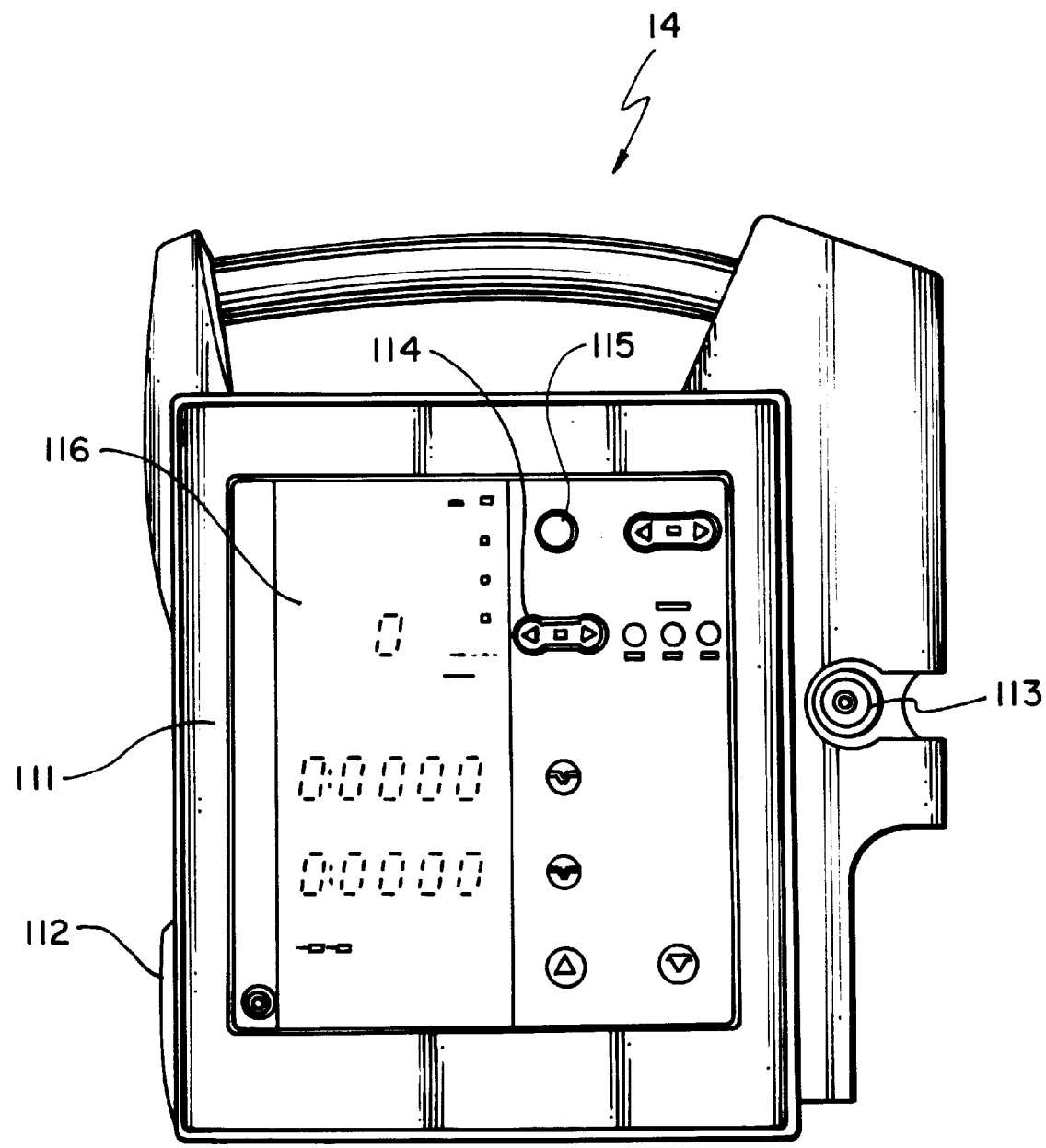
FIG. 5 shows an ultrasonic generator of the ultrasonic liposuction system of FIG. 1.

Referring to FIG. 5, a front panel 111 of ultrasonic generator 14 includes a connector 113 for electrically connecting to control line 24, an on/off switch 112, an ultrasonic generator on/off switch 115, an amplitude adjustment button 114 to vary the signal to handpiece 12, and an amplitude display 116. The magnitude of the amplitude is shown as a percentage of the maximum amplitude. For example, the amplitude obtained at the distal end of cannula 38 of FIG. 4 is typically about 3.5 mil, with a maximum obtainable amplitude of about 5.1 mil (130μ peak-to-peak). Higher amplitudes are obtainable. On the back of ultrasonic generator 14 is a connector (not shown) for electrically connecting control signal lines 430b, 436b, 454, 456, 458, 460 and 414b to infiltrator/irrigator 16 and control signal lines 416b, 432b, and 474 to aspirator 18.

Figure 6:
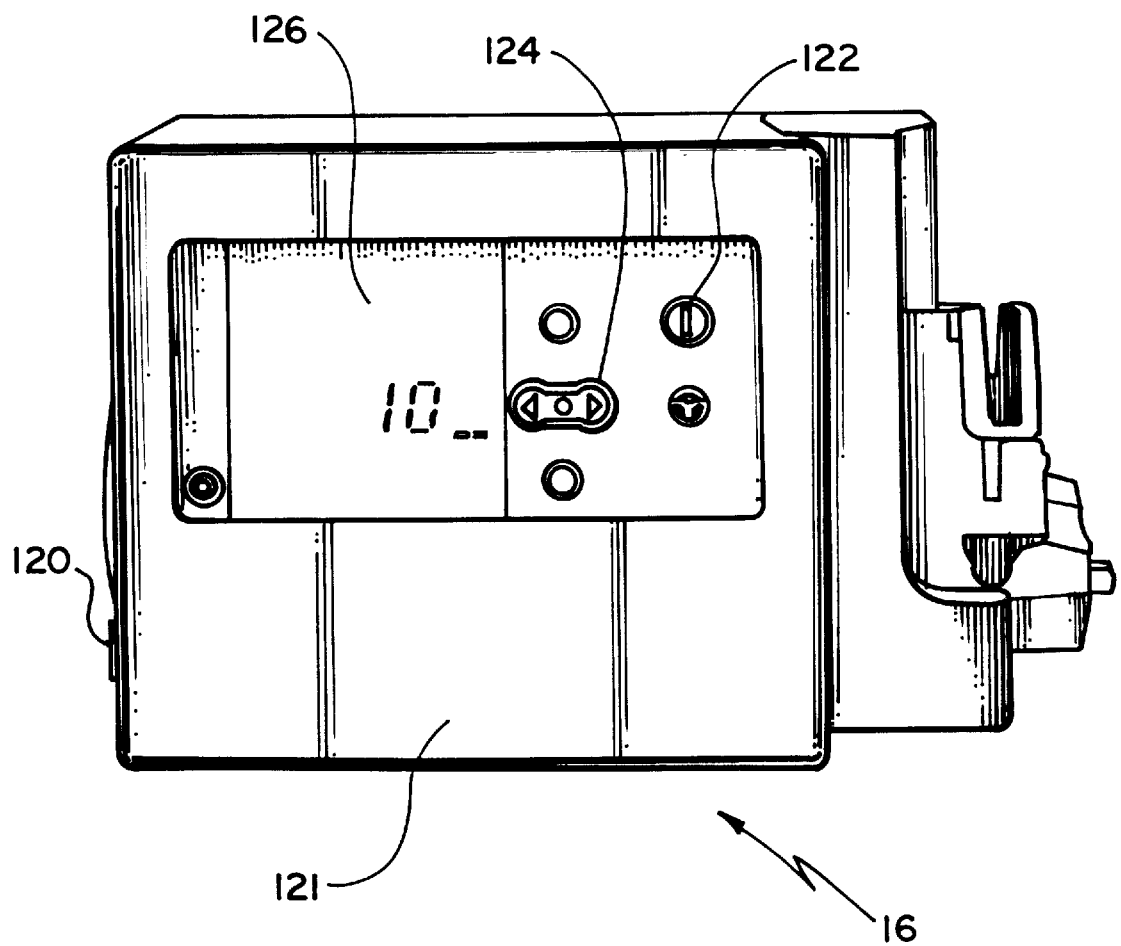
FIG. 6 shows an infiltrator/irrigator of the ultrasonic liposuction system of FIG. 1.

Referring to FIG. 6, infiltrator/irrigator 16 includes a front panel 121 with an on/off switch 120, an infiltration start/stop button 122, an infiltration/irrigation rate control button 124, and an infiltration/irrigation rate display 126. On/off switch 120 controls the activation and deactivation of infiltrator/irrigator 16, and control button 124 enables the user to vary the rate at which the infiltration/irrigation solution is supplied. Rate display 126 displays to the user the set supply rate.

Figure 7:
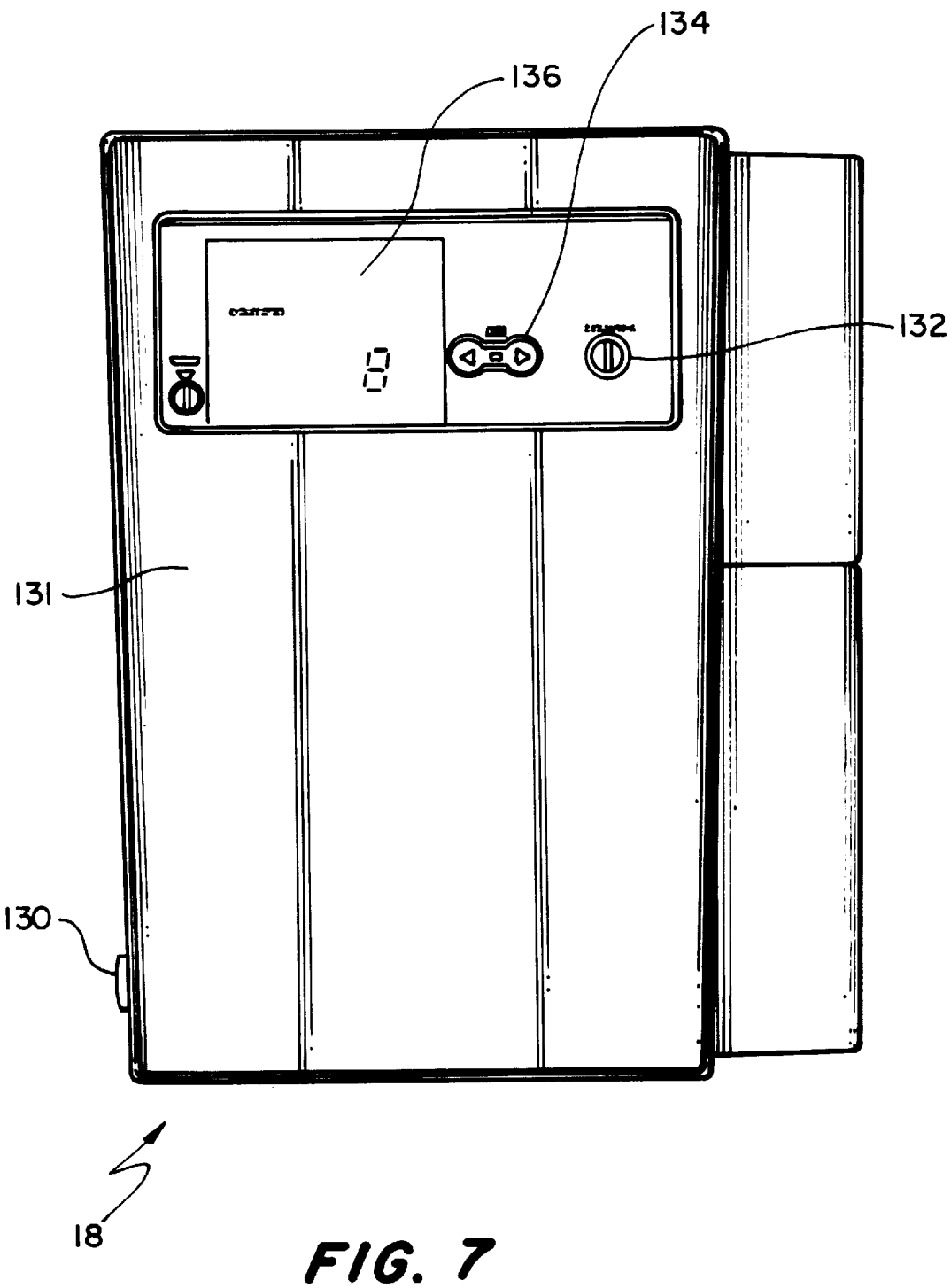
FIG. 7 shows an aspirator of the ultrasonic liposuction system of FIG. 1.

Referring to FIG. 7, a front panel 131 of aspirator 18 includes an on/off switch 130, an aspiration start/stop button 132, a vacuum level control switch 134, and a vacuum level display 136. On/off switch 130 activates and deactivates power to aspirator 18, while start/stop button 132 activates and deactivates pump 40 (FIG. 2). Control switch 134 is used to alter the amount of suction applied at the surgical site, and the applied suction is displayed on vacuum level display 136.

Figure 8:
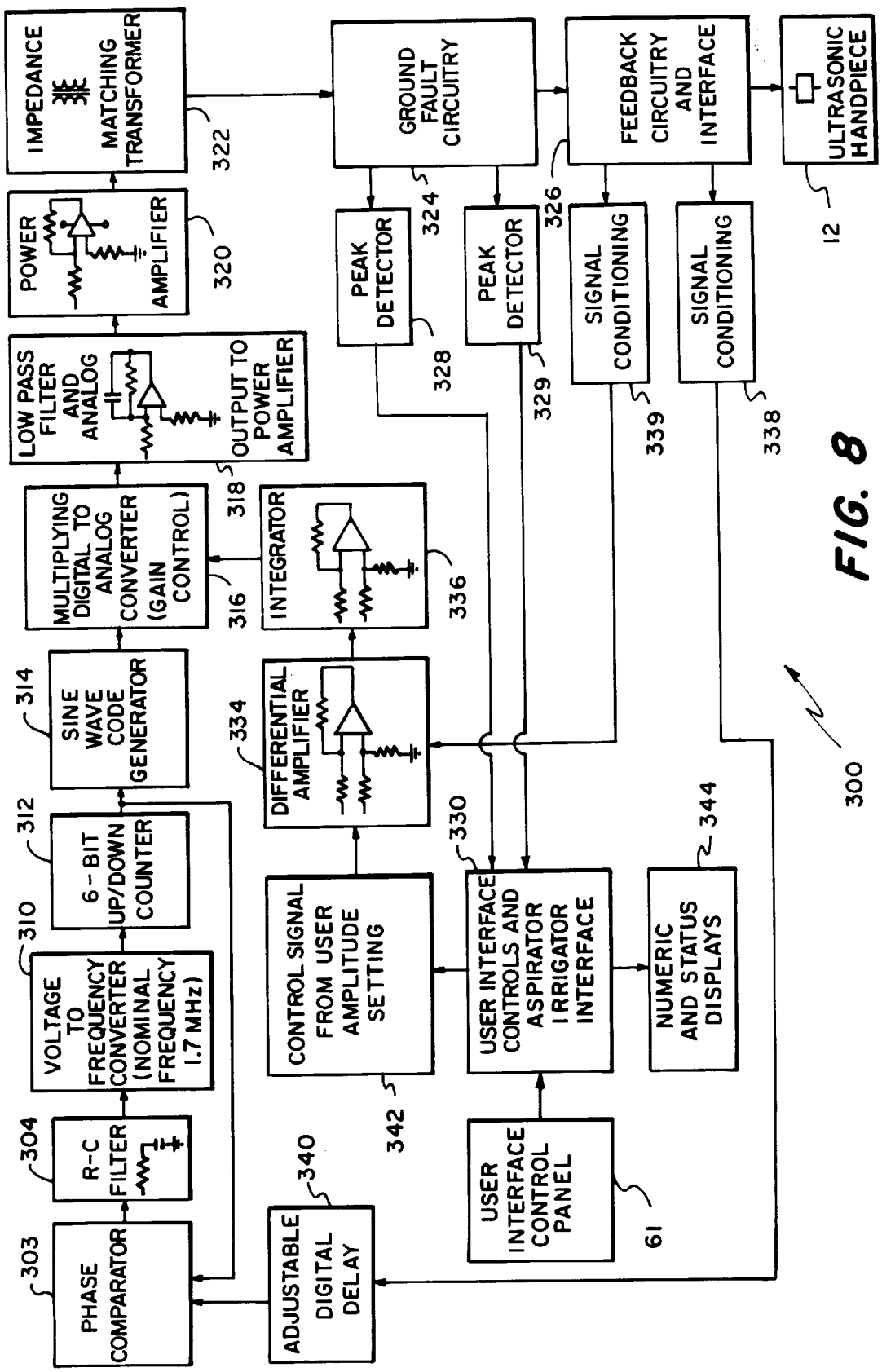
FIG. 8 is a block diagram of a phase lock loop, constant amplitude control system of the ultrasonic liposuction system of FIG. 1.

Referring to FIG. 8, a phase lock loop (PLL), constant amplitude control system 300 of ultrasonic liposuction system 10 provides for amplitude control and frequency control of cannula 38.

Amplitude control maintains a constant motional current through transducer 36 of handpiece 12. Since the amplitude of cannula 38 is directly proportional to the motional current, the constant motional current ensures that the amplitude of the cannula remains constant. It is desirable that the amplitude remain constant because the amplitude is proportional to the fragmenting power of the ultrasonically vibrating cannula. Amplitude control circuit compensates for changes in impedance of the transducer due to variations in the load on the transducer.

Frequency control maintains cannula 38 at its optimum resonant frequency. The cannula must run in mechanical resonance to efficiently emulsify the tissue. Frequency control compensates for changes in the resonant frequency of cannula 38, for example, due to losses in the system, changes in the ambient temperature, or changes in the load tolerances of cannula 38 or transducer 36.

Control system 300 uses the output of a voltage to frequency converter 310 to drive a 6 bit up/down counter 312. The output of counter 312 is used to generate addressing codes for an EPROM (sine wave code generator) 314. The signal from generator 314 is sent into a multiplying digital to analog converter 316 with gain control. Converter 316 produces a representation of an analog sine wave which is sent through a low pass filter 318 to eliminate any high frequency noise. The analog output from filter 318 is sent to a 500 watt linear amplifier 320. The output from amplifier 320 is sent to an impedance matching transformer 322. Transformer 322 acts to step-up the voltage and to match the impedance of transducer 36 to amplifier 320.

The signal path between transformer 322 and transducer 36 is monitored by a ground fault circuit 324 and a feedback interface circuit 326. Ground fault circuit 324 is used to monitor the integrity of the ground wires that run from transducer 36 to ultrasonic generator 14. A user interface controller 330 (for ultrasonic generator 14, infiltrator 16, and aspirator 18) combines the output signals from a pair of peak detectors 328, 329, which receive signals from ground fault circuit 324. Controller 330 sends a signal to numeric and status displays 344 to display the condition of the ground wires. Ground fault circuit 324 is used as a fail-safe for transducer 36, and is independent from the amplitude and frequency control.

For amplitude control, an output from ground fault circuit 324 is also fed into the feedback circuitry 326. Feedback circuitry 326 includes two current transformers disposed within ultrasonic generator 14. One transformer monitors the current through transducer 36. This current is signal conditioned at 339 and subsequently fed into a differential amplifier 334 which compares the conditioned current to the amplitude signal 342 set by the user via control pad 61 to regulate the current through the amplitude control to maintain a constant amplitude. The output of differential amplifier 334 is sent into an integrator 336 which controls the response time of the amplitude control. The output of integrator 336 is fed into multiplying digital to analog converter 316. The level of this signal is multiplied with the binary code generated by sine wave code generator 314 to control the gain of digital to analog converter 316. This gain control regulates the current through the transducer by increasing the amplitude of the sine wave sent to power amplifier 320 when more energy is needed to provide a constant current through the amplitude control, or decreasing the amplitude of the sine wave when less energy is needed, thereby ensuring that the tip of cannula 38 vibrates at a constant amplitude.

For frequency control, the resonant frequency of transducer 36 is determined by comparing the phase of the voltage across transducer 36 to that of the current in the transducer. The output of feedback circuitry 326 is amplified and conditioned at 338 to provide digital phase information representing the current in the transducer. The phase information of the current is sent to an adjustable digital delay 340. The output of digital delay 340 is fed into a phase comparator 303. A portion of the output from 6 bit up/down counter 312 which represents the voltage across transducer 36 is also input to phase comparator 303. Thus phase comparator 303 compares the phase of the voltage of transducer 36 to the phase of the current through transducer 36. The phase difference between the current in the transducer and the voltage across the transducer should be 0° when transducer 36 is operating at its resonant frequency. Digital delay 340 is set so that when transducer 36 is operating at its resonant frequency, the current signal from digital delay 340 and the voltage signal from counter 312 are in phase.

The output of phase comparator 303 is sent through a RC filter 304 to filter the output of comparator 303 from a square wave signal to a DC level. The output of RC filter 304 is then fed into voltage to frequency converter 310 (with a nominal frequency of 1.7 MHz) to complete the phase lock loop so that the resonant frequency of transducer 36 can be tracked. The frequency control maintains transducer 36 at the appropriate resonant frequency.

User interface control panel, e.g. control pad 61, is used to send user input information to user interface controller 330 to provide centralized control of ultrasonic liposuction system 10 so that the surgeon does not need to individually adjust ultrasonic generator 14. The surgeon is able to activate and deactivate ultrasonic generator 14, as well as vary the ultrasonic amplitude of ultrasonic generator 14, with control pad 61 via controller 330. Infiltrator/irrigator 16 and aspirator 18 are also interfaced with controller 330. The setting and status of the components of ultrasonic liposuction system 10 are displayed on numeric and status displays 344.

During surgery, a surgeon advances a non-ultrasonically vibrating cannula (not shown) connected to a non-ultrasonic handpiece to the area to be treated. The surgeon activates infiltrator/irrigator 16 using foot control device 22 to provide an infiltration solution to the entire area to be treated. The infiltration procedure is terminated by deactivating infiltrator/irrigator 16 with foot control device 22. The non-ultrasonic cannula is then withdrawn from the patient and removed from handpiece 12. Alternatively, the non-ultrasonically vibrating cannula can be connected to handpiece 12 to enable the surgeon to activate and deactivate the infiltration procedure with start/stop button 68 on handpiece 12.

The surgeon attaches cannula 38 and sheath 72 to handpiece 12 and advances cannula 38 and sheath 72 to the surgical site. Ultrasonic generator 14 is activated by pressing start/stop button 62 on handpiece 12. The surgeon manipulates the cannula within the body cavity to selectively treat tissue to be removed. The surgeon adjusts the amplitude of the ultrasonic vibrations with amplitude increase and decrease buttons 64 and 66, respectively. During the procedure, an irrigation saline solution can be provided by activating infiltrator/irrigator 16 with start/stop button 68, and the rate at which the irrigation solution is supplied can be varied with rate control button 124 on front panel 121 of infiltrator/irrigator 16. Aspiration is provided by activating aspirator 18 with aspirator start/stop button 70. The amount of suction applied at the surgical site can be varied with vacuum level control switch 134 on front panel 131 of aspirator 18. Alternatively, irrigation and aspiration can be controlled with foot control device 22. The vacuum level of the aspirator and the irrigation, as well as the infiltration, rate may be controlled with switches on the handpiece.

In the illustrated embodiment, ultrasonic generator 14, infiltrator/irrigator 16, and aspirator 18 are controlled in an integrated manner with handpiece 12. Ultrasonic generator 14, infiltrator/irrigator 16 and aspirator 18, however, may each be used as a stand-alone unit, whereby the control inputs are provided by using the control buttons and switches on the respective front panels of the individual units.

Other embodiments are within the scope of the following claims.

What is claimed is:

1. An ultrasonic liposuction system comprising:
   a handpiece including a transducer for converting electrical energy into mechanical energy in the form of ultrasonic vibrations,
   an ultrasonic generator electrically connected to the handpiece for supplying the electrical energy to the transducer,
   an aspirator connected in fluid communication with the handpiece for providing aspiration at a surgical site,
   a fluid source connected in fluid communication with the handpiece that provides a fluid at the surgical site, and
   a user interface disposed on the handpiece coupled to said ultrasonic generator, said aspirator, and said fluid source for generating control signals therefor.

2. The ultrasonic liposuction system of claim 1 wherein said user interface includes a control pad for generating said control signals.

3. The ultrasonic liposuction system of claim 1 wherein the user interface includes an input device for generating start/stop control signals for the ultrasonic generator.

4. The ultrasonic liposuction system of claim 1 wherein the user interface includes an input device for generating control signals to cause the ultrasonic generator to vary an amplitude of said ultrasonic vibrations.

5. The ultrasonic liposuction system of claim 4 wherein the input device includes a button for generating ultrasonic amplitude increase control signals for the ultrasonic generator.

6. The ultrasonic liposuction system of claim 4 wherein the input device includes a button for generating ultrasonic amplitude decrease control signals for the ultrasonic generator.

7. The ultrasonic liposuction system of claim 1 further including an ultrasonic generator control line connecting the user interface to the ultrasonic generator for transmitting control signals to said ultrasonic generator.

8. The ultrasonic liposuction system of claim 1 wherein the user interface includes an input device for generating start/stop control signals for the fluid source.

9. The ultrasonic liposuction system of claim 1 further including a fluid source control line connecting the user interface to the fluid source for transmitting control signals to said fluid source.

10. The ultrasonic liposuction system of claim 1 wherein the user interface includes an input device for generating start/stop control signals for the aspirator.

11. The ultrasonic liposuction system of claim 1 further including an aspirator control line connecting the user interface to the aspirator for transmitting control signals to said aspirator.

12. The ultrasonic liposuction system of claim 1 wherein said user interface further includes a foot control device for generating control signals for the ultrasonic generator, fluid source, and aspirator.

13. The ultrasonic liposuction system of claim 12 further including an ultrasonic generator control line connecting the foot control device to the ultrasonic generator for transmitting control signals to said ultrasonic generator.

14. The ultrasonic liposuction system of claim 12 further including a fluid source control line connecting the foot control device to the fluid source for transmitting control signals to said fluid source.

15. The ultrasonic liposuction system of claim 12 further including an aspirator control line connecting the foot control device to the aspirator for transmitting control signals to said aspirator.

16. The ultrasonic liposuction system of claim 12 wherein the foot control device is capable of simultaneously activating the ultrasonic generator, fluid source, and aspirator.

17. The ultrasonic liposuction system of claim 1 wherein said user interface further includes a foot control device for generating control signals for the fluid source, wherein the fluid source is an infiltrator.

18. The ultrasonic liposuction system of claim 1 wherein the ultrasonic generator includes a front panel having an amplitude display, an amplitude adjustment switch, a power on/off switch, an ultrasonic generator on/off switch, and a connector for connecting the ultrasonic generator to the handpiece.

19. The ultrasonic liposuction system of claim 1 wherein the aspirator includes a front panel having a power on/off switch, an aspiration start/stop button, a vacuum level control button, a vacuum level display, and a connector for connecting the aspirator to the ultrasonic generator.

20. The ultrasonic liposuction system of claim 1 wherein the fluid source includes a front panel having a power on/off switch, a fluid source start/stop button, a fluid source flow rate control button, a fluid source flow rate display, and a connector for connecting the fluid source to the ultrasonic generator.

21. The ultrasonic liposuction system of claim 1 wherein the ultrasonic vibrations have a frequency from about 15 KHz t o about 60 KHz.

22. The ultrasonic liposuction system of claim 21 wherein the ultrasonic vibrations have a frequency of about 27 KHz.

23. The ultrasonic liposuction system of claim 1 wherein the fluid source includes a pump.

24. The ultrasonic liposuction system of claim 1 wherein the aspirator includes a canister configured to collect matter removed from the surgical site.

25. The ultrasonic liposuction system of claim 24 wherein the aspirator includes a filter located downstream of the canister.

26. The ultrasonic liposuction system of claim 1 further including a feedback system for controlling the frequency and amplitude of the ultrasonic vibrations.

27. The ultrasonic liposuction system of claim 1 wherein the ultrasonic transducer includes a piezoelectric crystal.

28. The ultrasonic liposuction system of claim 27 wherein the piezoelectric crystal generates ultrasonic vibrations with a frequency from about 15 KHz to about 60 KHz.

29. The handheld surgical apparatus of claim 28 wherein the piezoelectric crystal generates ultrasonic vibrations with a frequency of about 27 KHz.

30. The ultrasonic liposuction system of claim 1 wherein the ultrasonic generator and the aspirator are disposed on a movable cart.

31. A handheld surgical apparatus for use with an ultrasonic liposuction system comprising:
   a handpiece electrically connected to an ultrasonic generator and an aspirator, and configured to receive an ultrasonic probe,
   an ultrasonic transducer disposed within the handpiece for converting electrical energy from the ultrasonic generator into mechanical energy in the form of ultrasonic vibrations,
   an aspirator conduit disposed within the handpiece,
   a fluid conduit disposed within the handpiece, the fluid conduit in liquid communication with a fluid source, and
   a user interface disposed on the handpiece and coupled to said ultrasonic generator, said aspirator, and said fluid source for generating control signals therefor.

32. The handheld surgical apparatus of claim 31 wherein the aspirator conduit includes a proximal end terminating in an aspirator connector for connecting with the aspirator, and a distal end configured for connection in fluid communication with the probe so that matter can be removed from a surgical site by suction provided by the aspirator.

33. The handheld surgical apparatus of claim 31 wherein the user interface includes an input device for generating start/stop control signals for the ultrasonic generator.

34. The handheld surgical apparatus of claim 31 wherein the user interface includes an input device for generating control signals to cause the ultrasonic generator to vary an amplitude of said ultrasonic vibrations.

35. The handheld surgical apparatus of claim 34 wherein the input device includes a button for generating ultrasonic amplitude increase control signals to the ultrasonic generator.

36. The handheld surgical apparatus of claim 34 wherein the input device includes a button for generating ultrasonic amplitude decrease control signals for the ultrasonic generator.

37. The handheld surgical apparatus of claim 31 wherein the user interface includes an input device for generating start/stop control signals for the aspirator.

38. The handheld surgical apparatus of claim 31 wherein the fluid conduit has a proximal end terminating in a fluid source connector for connecting with the fluid source, and a distal end configured to provide a fluid supplied by the fluid source to the probe and subsequently to the surgical site.

39. The handheld surgical apparatus of claim 38 wherein the user interface includes an input device for generating start/stop control signals for the fluid source.

40. The handheld surgical apparatus of claim 31 wherein the probe is a cannula.

41. A method of controlling an ultrasonic liposuction system comprising:
   providing a handpiece that includes a user interface, the user interface being coupled to an ultrasonic generator, an aspirator, and a fluid source for generating control signals therefor,
   activating the ultrasonic generator with a first input device on the user interface,
   activating the aspirator with a second input device on the user interface to provide suction,
   activating a fluid source with a third input device on the user interface to provide fluid to a surgical site.

42. The method of claim 41 further including controlling the amplitude of the ultrasonic generator with a fourth input device on the user interface.

43. A method of performing liposuction comprising:
   advancing a probe and a sheath disposed coaxially about the probe to a surgical site,
   ultrasonically vibrating the probe to treat tissue at the surgical site by activating an ultrasonic generator connected to the probe, aspirating the surgical site by applying suction to the surgical site to remove the treated tissue by activating an aspirator connected to the probe, irrigating the site with fluid from a fluid source, and controlling activation of the ultrasonic generator, the aspirator, and the fluid source with a user interface coupled to the ultrasonic generator, the aspirator, and the fluid source, wherein the user interface is disposed on a handpiece connected to the probe.

44. The method of claim 43 wherein fluid supplied by said fluid source flows in a space defined between the probe and the sheath.

* * * * *